United States Patent [19]

Milstein

[11] Patent Number: 5,034,534
[45] Date of Patent: Jul. 23, 1991

[54] PROCESS FOR PRODUCING SACCHARIN, SACCHARIN ANALOGUES OR THEIR SALTS

[75] Inventor: David Milstein, Rehovot, Israel

[73] Assignee: E. I. du Pont de Nemours and Company, Wilmington, Del.

[21] Appl. No.: 424,005

[22] Filed: Oct. 19, 1989

Related U.S. Application Data

[63] Continuation-in-part of Ser. No. 219,272, Jul. 15, 1988, abandoned.

[51] Int. Cl.$^5$ ............................................. C07D 275/06
[52] U.S. Cl. ..................................... 548/210; 548/211
[58] Field of Search ................................ 548/210, 211

[56] References Cited

U.S. PATENT DOCUMENTS

| | | | |
|---|---|---|---|
| 4,379,769 | 4/1983 | Levitt | 260/545 R |
| 4,581,178 | 4/1986 | Milstein | 558/409 |
| 4,764,239 | 8/1988 | Jacobine et al. | 548/210 X |

FOREIGN PATENT DOCUMENTS 8700536 1/1987 PCT Int'l Appl. ................. 548/210

OTHER PUBLICATIONS

Schoenberg et al., J. Org. Chem., vol. 39, No. 23, pp. 3327-3331 (1974).
Dieck et al., J. Org. Chem., vol. 40, pp. 2819-2822 (1975).
Mori et al., J. Org. Chem., vol. 43, No. 9. pp. 1684-1687 (1978).
Mori et al., Heterocycles, vol. 12, No. 7, pp. 921-924 (1979).
Heck, "Palladium Reagents in Organic Synthesis," Academic Press, New York, pp. 352-353 (1985).
Brunet et al., J. Org. Chem., vol. 48, No. 8, pp. 1166-1171 (1983).
Foa et al., J. of Organometallic Chem., vol. 285, pp. 293-303 (1985).
Dolle et al., J. Chem. Soc. Commun., pp. 904-905 (1987).
Cacchi et al., Tetrahedron Letters, vol. 27, No. 33, pp. 3931-3934 (1986).
Lombardino, J. Org. Chem., vol. 36, No. 13 (1971), pp. 1843-1845.

*Primary Examiner*—Diana Rivers

[57] ABSTRACT

This invention concerns a new process for the catalytic carbonylation of certain aryl halides or aryl tosylates to amides by use of a complex of palladium and at least one ligand. More specifically, the invention concerns carbonylation of halogenoaromaticsulfonamides or tosylatoaromaticsulfonamides to saccharin, saccharin analogues or their salts.

19 Claims, No Drawings

PROCESS FOR PRODUCING SACCHARIN, SACCHARIN ANALOGUES OR THEIR SALTS

CROSS-REFERENCE TO RELATED APPLICATION

This is a continuation-in-part application of copending U.S. Pat. application Ser. No. 07/219,272 filed Jul. 15, 1988.

BACKGROUND OF THE INVENTION

1. Field of the Invention

This invention relates to a new process for catalytic carbonylation of certain aryl halides and/or aryl tosylates to amides and, in particular, where the aryl halides and/or aryl tosylates comprise 2-halobenzenesulfonamide(s) and/or 2-tosylatobenzenesulfonamide(s), the catalyst includes a complex comprising palladium and at least one alkyl phosphine ligand and the amides are saccharin, at least one saccharin analogue or at least one of their salts.

2. Description of Related Art

Examination of publications shows that considerable time and interest have been devoted to the carbonylation of aryl halides.

Palladium complexes are reported to catalyze combination of aryl (Ar), heterocyclic and vinylic bromides and iodides with carbon monoxide, a primary or secondary amine, and a tertiary amine to produce amides according to the formula:

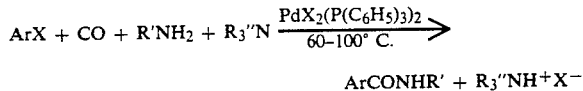

$$ArX + CO + R'NH_2 + R_3''N \xrightarrow[60-100° C.]{PdX_2(P(C_6H_5)_3)_2} ArCONHR' + R_3''NH^+X^-$$

where X is Br or I. See A. Schoenberg et al., "Palladium-Catalyzed Amidation of Aryl, Heterocyclic, and Vinylic Halides," J. Org. Chem., Vol. 39, No. 23, pages 3327-3331 1974. Several palladium complexes have been used in carbonylation reactions to catalyze aryl halide (ArX) carbonylation, where X is Br, and I. See M. Mori et al., "Reactions and Synthesis with Organometallic Compounds.7. Synthesis of Benzolactams by Palladium-Catalyzed Amidation" is disclosed in J. Org. Chem., Vol. 43, No. 9, pages 1684-1687, 1978.

More recently, it has been published that only aryl bromides and iodides undergo a carbonylation reaction of an aryl halide in the presence of a catalyst containing palladium. See R. F. Heck, "Palladium Reagents in Organic Synthesis," Academic Press, New York, pages 352-353, 1985.

It is also known that one can carbonylate aryl halides in the presence of a catalyst including cobalt acccording to the formula

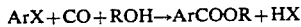

$$ArX + CO + ROH \rightarrow ArCOOR + HX$$

where X is Br or Cl. However, the only reported chloroaromatic compounds that undergo carbonylation in a cobalt-catalyzed reaction are activated chloronaphthalenes and 4-chlorobenzoic acid. Further, they yielded esters, not amides. See M. Foa et al., "Cobalt-Catalyzed Carbonylation of Aryl Halides," J. Organometallic Chem., Vol. 285, pages 293-303, 1985. In fact, one chloroaromatic compound, specifically 1,2-dichlorobenzene, is disclosed as useable as an inert solvent in cobalt-catalyzed carbonylation of aryl halides. See Burnet et al., "Sunlamp-Irradiated Phase-Transfer Catalysis. Cobalt Carbonyl Catalyzed Srn1 Carbonylations of Aryl and Vinyl Halides," J. Org. Chem., Vol. 48, No. 8, pages 1166-1171, 1983. Cacchi et al., "Palladium-Catalyzed Carbonylation of Aryl Triflates" (1986), describes catalysis under conditions in which aryl chlorides do not react.

It is an object of the present invention to provide for the carbonylation of chlorobenzenesulfonamides or tosylatobenzenesulfonamides as potentially commercially valuable reactions. An advantage of the present invention is the reactions are easily carried out and the reagents involved are not expensive, so that the reactions could be used to transform inexpensive industrial materials to higher commercial value derivatives. A feature of the present invention is that it is used in the carbonylation of aryl halides or aryl tosylates to yield saccharin, saccharin analogues and their salts. Such reactions advantageously enable one to select from a variety of aryl halides including chloride, bromide, and iodide, or aryl tosylates depending on the desired product. These products are for instance, intermediates in the synthesis of sulfonylurea herbicides These and other objects, features and advantages of the present invention will become apparent on having reference to the following description.

SUMMARY OF THE INVENTION

The present invention is directed to a process for producing saccharin, saccharin analogues or their salts.

More specifically, the invention comprises a process for producing at least one salt of saccharin and/or saccharin analogues, comprising reacting a compound selected from the group consisting of 2-halobenzenesulfonamide 2-tosylatobenzenesulfonamide and mixtures thereof with carbon monoxide and base in the presence of solvent inert to the reactants and catalyst comprising at least one complex of Pd(0) or Pd(II) or Pd(IV) with at least one $PR_6R_7R_8$ or $R_9R_{10}P(CH_2)_nPR_{11}R_{12}$ ligand wherein:

$R_6$ is alkyl of 1 through 16 carbons;

$R_7$, $R_8$, $R_9$, $R_{10}$, $R_{11}$ and $R_{12}$ are independently selected from hydrogen, alkyl of 1 through 8 carbons or aryl of 6 through 14 carbons, or alkylaryl of 7 through 14 carbons; and n is 2, 3 or 4.

Preferred reactant compounds are a mixture of 2-chlorobenzensulfonamide and 2-tosylatobenzenesulfonamide. A most preferred compound is 2-chlorobenzenesulfonamide.

DETAILED DESCRIPTION OF THE INVENTION

The present invention comprises a process for producing amides and, more specifically, saccharin, saccharin analogues or their salts.

More specifically, a saccharin salt or derivative may be produced as follows.

First, quantities of (1) 2-halobenzenesulfonamide(s) and/or 2-tosylatobenzenesulfonamide(s), (2) base, (3) solvent and (4) catalyst are placed in a suitable container or tube. The order of addition of the ingredients is not important. Preferably, this is accomplished in an oxygen free environment, such as in a nitrogen dry box. If accomplished in a nitrogen dry box, then the tube should be sealed in a way that permits stirring. Preferably, the resulting solution is thoroughly mixed, such as by stirring.

Regarding ingredient (1), any 2-halobenzenesulfonamide(s) and/or 2-tosylatobenzenesulfonamide(s) or mixtures thereof can be used as long as they are of the formula:

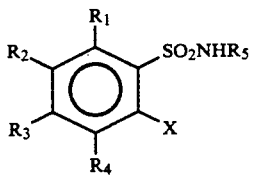

wherein:

X is Cl, Br, I or $O_3SC_6H_4CH_3$ (which is OTs where Ts is tosyl);

$R_1$, $R_2$, $R_3$ and $R_4$ are independently selected from hydrogen, alkyl of 1 through 9 carbons, F, Cl, Br, CN, $NO_2$, $OR_5$, $COR_5$, $CO_2R_5$, $SO_2R_5$ or aryl; and Alternatively any two adjacent $R_1$, $R_2$, $R_3$ or $R_4$ can be a fused ring such as benzo, with further appropriate substituents

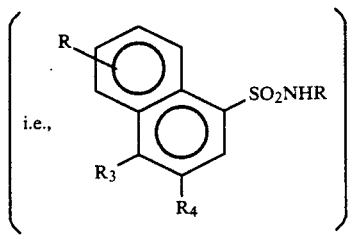

$R_5$ is hydrogen, alkyl of 1 through 16 carbons, aryl or alkylaryl, and R is independently $R_1$–$R_4$.

Throughout this description aryl is defined as a radical containing 6 through 14 carbon atoms and derived from an aromatic hydrocarbon by the removal of one hydrogen atom. Examples of aryls include phenyl ($C_6H_5$), naphthyl ($C_{10}H_7$), anthryl ($C_{14}H_9$), tolyl ($C_6H_4CH_3$) and other substituted aryls. Alkylaryl radicals suitable for the present invention include benzyl, phenyl ethyl, etc.

Examples of 2-halobenzenesulfonamides include 2-chlorobenzenesulfonamide, 2-chloro-6-methylbenzenesulfonamide or 2,5-dichlorobenzenesulfonamide, see, e.g., U.S. Pat. No. 4,426,318 column 2, lines 4–19. Examples of 2-tosylatobenzenesulfonamides include 2-tosyl-6-methylbenzenesulfonamide.

Concerning ingredient (2), the base is selected to receive a hydrogen chloride molecule from 2-halobenzenesulfonamide or a TsOH molecule derived from the 2-tosylatobenzenesulfonamide molecule. Preferably, the base is soluble in the employed solvent. Example bases that can be used and are soluble in preferred polar solvents include triethylamine ($N(C_2H_5)_3$), pyridine, piperidine, piperazine, $CH_3CO_2Na$, and other organic bases. Preferably, there are twice as many moles of base as moles of 2-halobenzene-sulfonamide and/or 2-tosylato-benzenesulfonamide, put into the tube.

Regarding ingredient (3), the solvent may be any solvent that is inert to the reactants and the catalyst. Preferably, the solvent and its amount are chosen such that all other ingredients in the tube can dissolve or are soluble in the solvent. Preferably, the amount of solvent is no more than necessary to dissolve the other ingredients so that a small reaction vessel can be used, the ingredients are not too diluted and the ingredients are given maximum contact with one another in the vessel. It is additionally preferred that the solvent be a polar solvent. Representative examples of useable solvents include toluene, dioxane, benzonitrile ($C_6H_5CN$), or acetonitrile ($CH_3CN$), where the latter three solvents are polar solvents.

With respect to ingredient (4), the catalyst comprises at least one complex of palladium with a valence of zero (0) or plus two (+2) (i.e., Pd(O) or Pd(II), respectively) with at least one ligand. Alternatively, a complex of palladium with a valence of plus four (+4) (i.e., Pd IV) can be used; it will be reduced to another complex to be active Illustrative complexes that catalyze the reaction of the present invention that include Pd(0) are $Pd(P(CH_3)(C_6H_5)_2)_4$, $Pd(P(CH_3)_3)_4$ and $Pd((C_6H_5)_2PCH_2CH_2CH_2P(C_6H_5)_2)_2$. Illustrative complexes including Pd(II) are $Pd((C_6H_5)_2PCH_2CH_2CH_2P(C_6H_5)_2)Cl_2$, $Pd(P(CH_3)(C_6H_5)_2)_2Cl_2$, $Pd(CH_3CN)_4(BF_4)_2$ or palladium acetate ($Pd(OCOCH_3)_2$), the latter two requiring an additional ligand, i.e., 1,3-bis(diphenylphosphino)propane to catalyze the reaction of the present invention. An illustrative complex including Pd(IV), for example, $Na_2PdCl_6$, is useful because it will be reduced to Pd(0) under reaction conditions.

The catalyst may include more than one ligand. The ligands may be bound and/or added to the palladium. By "bound" is meant linked to the palladium, such as using $Pd(P(CH_3)_3)_4$ as the catalyst. "Added" means inserting palladium into the tube separate from the ligand(s), such as adding a palladium salt (e.g., $Pd(OCOCH_3)_2$) and then $(C_6H_5)_2PCH_2CH_2CH_2P(C_6H_5)_2$ separately into the tube. Representative example $PR_6R_7R_8$ ligands include $PCH_3(C_6H_5)_2$, $P(CH_3)_3$ or $P(n-C_4H_9)_3$. Representative $R_9R_{10}P(CH_2)_nPR_{11}R_{12}$ ligands include 1,2-bis(diphenylphosphino)ethane or dppe (where n is 2; and $R_9$, $R_{10}$, $R_{11}$ and $R_{12}$ are $C_6H_5$); 1,3-bis(diphenyl-phosphino)propane or dppp (where n is 3; and $R_9$, $R_{10}$, $R_{11}$ and $R_{12}$ are $C_6H_5$) and 1,4-bis(-diphenyl-phosphino)butane or dppb (where n is 4; and $R_9$, $R_{10}$, $R_{11}$ and $R_{12}$ are $C_6H_5$). As indicated by these examples, n may be the number 2, 3 or 4, but it is preferably 3 or 4, and most preferably 3. $R_7$–$R_{12}$ may include a variety of commercially available substituents.

Preferably, the catalyst is supported on a polymer. Any polymer can be used as long as it adequately supports the catalyst and does not interfere with the reaction. An example of a polymer is phosphine modified polystyrene, see, e.g., U.S. Pat. No. 4,426,318. Use of polymer support enables the support plus the catalyst to be easily separated from the solution after the reaction, for reuse.

A suitable catalyst supported on a polymer for use in the present invention may be prepared as follows. First, one prepares a polymer supporting phosphine molecules. Second, one bonds palladium or palladium bound to at least one ligand to the polymer bound phosphine molecules to produce a polymer supported catalyst.

The first step may be accomplished by reacting at least one alkali metal with phosphine molecules in the presence of a dry solvent to form a precipitate. The alkali metal can be Li, Na, K, Rb, Cs or Fr and, preferably, it is K. Representative examples of suitable phosphine molecules include dppe and preferably dppp. The solvent should be "dry" or without water so that it does not react with the alkali metal. Further, preferably at least the phosphine dissolves in the solvent. Example solvents include dry dioxane, dry diethyl ether or dry tetrahydrofuran (THF), where THF is the preferred solvent.

The mixture or suspension should be stirred to suspend the precipitate. If excess or unreacted potassium (K) remains in the mixture after the reaction, the mixture can be placed in an oxygen free environment, such as in a nitrogen glove box and the unreacted potassium removed, such as by decantation.

The suspension can then be combined with a slurry of brominated polymer in a solvent, such as a quantity of the solvent already in the suspension. Illustrative brominated polymers include brominated ethylene/styrene copolymers or brominated polystyrene, the latter being preferred. The resulting mixture may be stirred.

Unreacted phosphine molecules can be hyrolyzed such as with deoxygenated acetone and water, or just water. Resin beads result which are preferably washed with one or more solvents including acetone, water, benzene, methanol or mixtures thereof. The resulting resin beads comprise phosphine molecules bound to a polymer.

Then palladium or palladium bound to at least one ligand is combined and reacted with the phosphine molecules bound to the polymer in the presence of a solvent. Example complexes including palladium bound to at least one ligand comprise $PdCl_2$ or palladium acetate $(Pd(OCOCH_3)_2)$, the latter being preferred. Representative solvents include benzene and toluene, or mixtures with THF or acetonitrile. This mixture may be stirred. Then the polymeric material may be filtered out from the filtrate and, if desired, washed with one or more solvents including benzene, THF, ether or mixtures thereof. The polymeric material may be dried, such as under a vacuum, resulting in a catalyst supported on a polymer for use and reuse in the process of the present invention.

After inserting the ingredients into the tube, carbon monoxide (CO) is added to the tube or the gas in the tube is replaced with carbon monoxide. The gas may be replaced by cooling the mixed solution to a convenient temperature to minimize vaporization of the solution ingredients and then evacuating gas from the tube one or more times. Then carbon monoxide can be added to the tube. Alternatively, carbon monoxide can be blown into the tube, flushing out the other gas. Carbon monoxide can be bubbled through the solution. Preferably, the tube is charged with 14 to 2000 pounds per square inch absolute (psia) of carbon monoxide at room temperature (or an equivalent pressure at other temperatures) and, more preferably, with 50 through 200 psia to ensure an excess amount of carbon monoxide for the reaction.

Then, the tube is preferably heated to a range of about 80° C. to about 250° C. and, more preferably, to the range of about 100° C. to about 150° C. to optimize the reaction conditions.

Periodically throughout the reaction the tube can be recharged or repressurized with carbon monoxide to the pressures identified above to ensure an excess amount of carbon monoxide. Preferably, the pressure of carbon monoxide is held constant during the reaction by continuous addition of carbon monoxide. Further, the contents of the tube can be mixed throughout the reaction or periodically throughout it to increase the rate of the reaction.

The above procedure may form a white crystalline precipitate which, if necessary, after cooling and venting the gas, can be removed by filtration from the filtrate. Additional solvent can now be added to facilitate the filtration. The precipitate can be washed one or more times, for instance, with water to redissolve products from the precipitate other than the salt $HN(C_2H_5)_3{}^+Cl^-$. Preferably, the quantities of the washing liquid are small and cold to minimize redissolving the salt $HN(C_2H_5)_3{}^+Cl^-$. The solvent and water can be removed from the filtrate under a vacuum, forming a residue which can be an oil depending on the ingredients used. The residue can be identified, such as, by Infrared Spectroscopy (IR), Proton Nuclear Magnetic Resonance (PNMR) or Mass Spectroscopy to be a saccharin salt or derivative.

In accordance with the present invention, saccharin and/or one or more saccharin analogues can be produced by reacting one or more salts of saccharin or one or more analogues of saccharin with an acid in the presence of a solvent.

More specifically, a compound selected from the group consisting of a salt of saccharin, a salt of a saccharin analogue and mixtures thereof with $[HN(C_2H_5)_3]^+$ is located in a reaction vessel or tube. This can be accomplished by removing the solvent and washing liquid from the filtrate from the aforesaid process for producing a salt of saccharin or a salt of a saccharin analogue. This can be accomplished by evaporation under a vacuum.

In addition, solvent is located in the tube to dissolve all other ingredients. Representative examples of solvents include water, methanol, dioxane or benzonitrile.

The solution can be mixed, filtered and concentrated under a vacuum, if desired. Concentrating the solution may be useful if one adds a large amount of solvent to more quickly dissolve the ingredients, but then wants to reduce the amount of solvent to increase contact of the ingredients in the solution.

In addition, at least one acid is located in the reaction tube. Representative examples of acids include hydrochloric acid, phosphoric acid, nitric acid, or sulfuric acid, preferably hydrochloric or sulfuric. If the acid is a gas, it can be bubbled through the solution, added to the tube or the gas in the tube can be replaced with the gaseous acid. Generally, if the acid is in an aqueous solution, the acid concentration may vary and the preferred acid concentration may vary significantly depending on the acid used. Preferably, the acid comprises an aqueous solution of hydrochloric acid with its concentration in the range of 30 through 40 percent by weight.

The order of adding the ingredients and the solvent has not been determined to be important.

A white precipitate is formed by this procedure. The precipitate can be isolated by filtration and washed one or more times with a washing liquid, for instance, with water to redissolve products from the precipitate other than the saccharin and/or saccharin analogue(s). Preferably, the quantities of the washing liquid are small and cold to minimize redissolving the salt $HN(C_2H_5)_3{}^+Cl^-$. The solvent and washing liquid can be removed from the filtrate, i.e., the precipitate can be dried under a vacuum, forming saccharin and/or saccharin analogue(s).

The following Examples illustrate the invention. All parts and percentages are by weight, and all degrees are Celsius, unless otherwise noted.

EXAMPLE 1

Carbonylation of 2-chlorobenzenesulfonamide with pd(PCH₃(C₆H₅)₂)₄

A 90 milliliter (mL) glass tube capable of being pressurized to at least 70 pounds per square inch atmospheric (psia) was charged in a nitrogen dry box with 0.5 grams (g) (2.6 millimoles (mmol)) of 2-chlorobenzene-sulfonamide, 0.588 g (5.2 mmol) of triethylamine (N(C₂H₅)₃ which is NEt₃), 0.2 g (0.22 mmol) of Pd(PCH₃(C₆H₅)₂)₄ and 6 mL of dioxane. The resulting solution was stirred at 25 degrees Celcius (° C.) for 30 minutes (min) and then cooled at −80° C., evacuated briefly and warmed up to room temperature. The tube was charged with 70 psia of carbon monoxide and heated at 150° C. overnight during which time a white crystalline precipitate formed. After cooling to room temperature, the pressure reading was 58 psia and the gas was vented. The precipitate was isolated by filtration and identified by Infrared Spectroscopy (IR) and proton Nuclear Magnetic Resonance (HNMR) as the salt HNEt₃ +Cl−. The solvent was removed from the filtrate under vacuum, and HNMR and IR of the residue showed quantitative formation of the saccharin derivative or salt A. The reaction of Example 1 can be illustrated by the general formula:

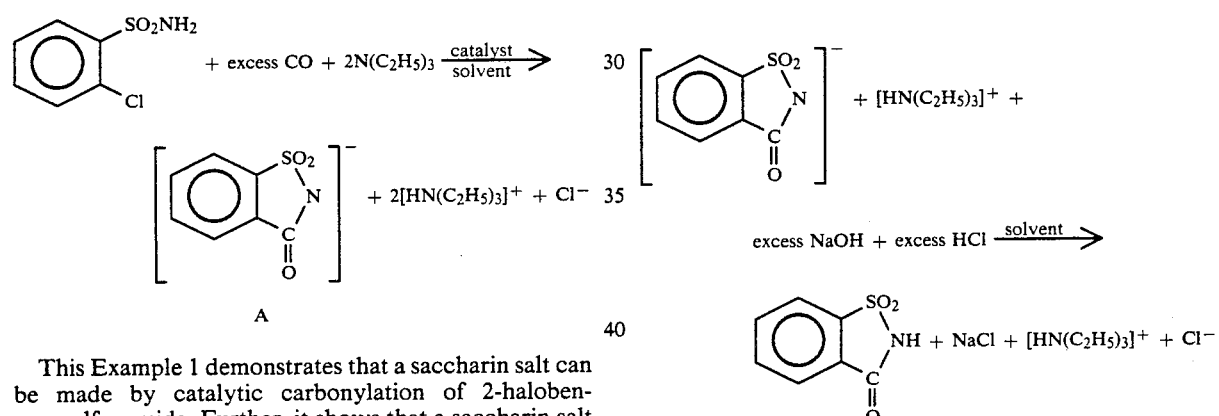

This Example 1 demonstrates that a saccharin salt can be made by catalytic carbonylation of 2-halobenzenesulfonamide. Further, it shows that a saccharin salt can be made using a catalyst including palladium plus a ligand to carbonylate a 2-halobenzene-sulfonamide. Further, it shows that a saccharin salt can be made using a catalyst including Pd(0) plus a ligand comprising Pd(PCH₃(C₆H₅)₂)₄ to carbonylate a 2-halobenzene-sulfonamide where the 2-halobenzenesulfonamide is of the formula:

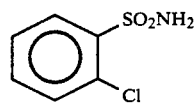

EXAMPLE 2

Carbonylation of 2-chlorobenzesulfonamide with Pd(CH₃CN)₄(BF₄)₂ and dppp.

A 90 mL glass pressure tube was charged in a nitrogen dry box with 2 g (10.4 mmol) of 2-chlorobenzenesulfonamide, 2.35 g (20.8 mmol) of triethylamine, 30 mg (0.067 mmol) of Pd(CH₃CN)₄(BF₄)₂, 30 mg (0.073 mmol) of 1,3-bis(diphenyl-phosphino)propane (dppp) and 6 mL of dioxane. The resulting suspension was stirred at room temperature for 30 min, cooled to −80° C., evacuated and charged with 70 psia of CO. After stirring at room temperature for 30 min, the tube was heated with stirring at 120° C. for 48 hours (hrs). Upon cooling to room temperature, the pressure was 38 psia and much solid formed. The pressure was released, 20 mL of dioxane were added to the reaction mixture to redissolve the solid, and the precipitate was isolated by filtration and washed with 5 mL of dioxane, three times, to yield 0.95 g of HNEt₃+Cl−. The reaction of Example 2 to this point can be also illustrated by the general formula provided in Example 1. The filtrate was combined with the washings and the solvent was removed in a vacuum to yield 2.84 g of almost pure saccharin salt A with [HN(C₂H₅)₃]+ and Cl−. To this material were added 60 mL of water followed by 1.6 g of NaOH. The resulting solution was filtered, concentrated under vacuum, and 4 g of HCl 38% by weight of the solution were added. A copious white precipitate was formed, and isolated by filtration and washed with a small amount of cold water. 1.73 g (91.4% of the calculated amount of saccharin expected based on the measured amounts of the ingredients) of pure saccharin was obtained after vacuum drying. This reaction step from the saccharin salt to saccharin is illustrated by the following general formula:

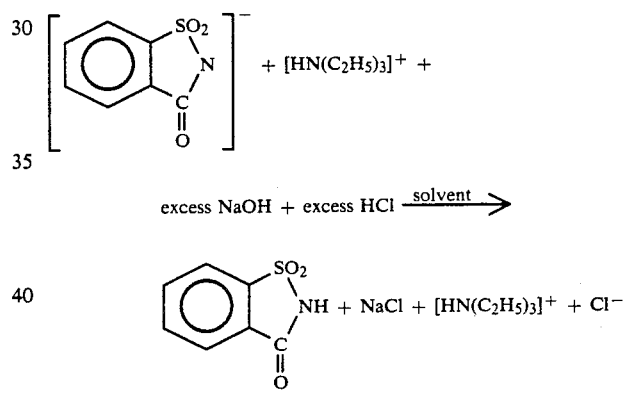

Like Example 1, this Example 2 demonstrates that a saccharin salt can be made by catalytic carbonylation of 2-halobenzenesulfonamide. Further, it shows that a saccharin salt can be made using a catalyst comprising a complex including palladium plus a ligand to carbonylate a 2-halobenzenesulfonamide. Further, it shows that a saccharin salt can be made using a catalyst including a complex including Pd(II) bound to a ligand (i.e., Pd(CH₃CN)₄(BF₄)₂) and adding another ligand (1,3-bis-(diphenylphosphino)propane (dppp)) to carbonylate a 2-halobenzenesulfonamide where the 2-halobenzenesulfonamide is of the formula:

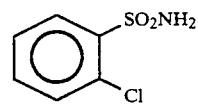

Further, Example 2 shows that one can use the saccharin salt produced by the process of the present invention to produce free saccharin by acidifying the saccharin salt.

EXAMPLE 3

Carbonylation of 2-chloro-6-methylbenzenesulfonamide 15 g (73 mmol) of 2-chloro-6-methylbenzenesulfonamide, 14.8 g (146 mmol) of triethylamine, 0.2 g (0.89 mmol) of palladium acetate, 0.37 g (0.89 mmol) of 1,3-bis(diphenylphosphino)propane and 45 mL of dioxane were placed in a 520 mL glass pressure tube under nitrogen. After cooling at 80° C. and evacuating, the tube was charged with 70 psia of CO and the contents were stirred at room temperature for 15 min. The solution was then heated with stirring for 16 hrs resulting in a pressure drop to 32 psi at room temperature. The tube was charged again with carbon monoxide to a pressure of 70 psia and heating with stirring for an additional 16 hrs, after which CO was added again to a pressure of 70 psia and the heating was continued for another 6 hrs (total heating time was 48 hrs). After cooling to room temperature, the pressure was released, 120 mL of dioxane were added and the precipitated $HN(C_2H_5)_3{}^+Cl^-$ was removed by filtration. The solvent was evaporated from the filtrate in a vacuum and to the resulting oil, which was mainly methylsaccharin salt B by IR and HNMR, were added 375 mL of water and a small amount of insoluble material were filtered off. To this solution were added 8 g of a 38% HCl by weight solution and the white precipitate was isolated after 30 min, was washed with 30 mL of water, and was dried in a vacuum to yield 11.3 g (70% of the calculated amount expected based on the measured amounts of the ingredients) of methylsaccharin, C, a saccharin analogue.

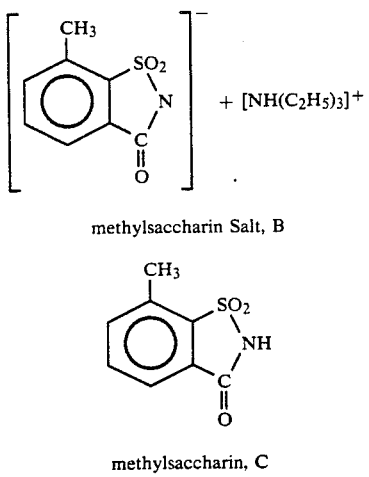

methylsaccharin Salt, B methylsaccharin, C

Example 3 demonstrates that using a 2-halobenzenesulfonamide with a methyl group (CH₃) in the sixth position on the phenyl ring produces methylsaccharin salt, B, and methylsaccharin, C, in accordance with the process of this invention. It further shows that use of a different complex catalizes the reaction, the catalyst comprising palladium acetate and 1,3-bis(diphenylphosphino)propane.

EXAMPLE 4

Carbonylation of 2,5-dichlorobenzenesulfonamide

A 90 mL glass pressure tube was charged in a nitrogen dry box with 2 g (8.84 mmol) of 2,5-dichlorobenzene-sulfonamide, 1.79 g (17.74 mmol) of triethylamine, 25 mg (0.11 mmol) of palladium acetate, 46 mg (0.28 mmol) of 1,3-bis(diphenylphosphino)propane and 6 mL of dioxane. After stirring at room temperature for 30 min, the suspension was cooled to −80° C. and the tube evacuated and charged with 70 psia of CO. The suspension was heated at 135° C. for 24 hrs and cooled to room temperature at which a pressure of 30 psi was observed. The gas was released, 20 mL of dioxane were added to the reaction mixture, and it was filtered to remove the precipitated $HN(C_2H_5)_3{}^+Cl^-$, which was washed with 5 mL, three times, of dioxane. The solvent was vacuum removed from the combined filtrate and washings and 30 mL of water were added to the residue. The resulting suspension was filtered, and the insolubles were washed with 5 mL of water. To the combined filtrate and washings were added 0.6 g of a 38% by weight solution of HCl. The mixture was stirred for 2 hrs and the white solid which formed was isolated by filtration, washed with 5 mL of water and dried in a vacuum. Gas Chromatography Mass Spectroscopy (GC-MS) analysis revealed that this solid consists of 92% of chlorosaccharin, D, 6% of 2-chloro-benzenesulfonamide and 2% of 2,5-dichlorobenzene-sulfonamide. A 42% yield of chlorosaccharin, D, based on the starting 2,5-dichlorobenzenesulfonamide was obtained.

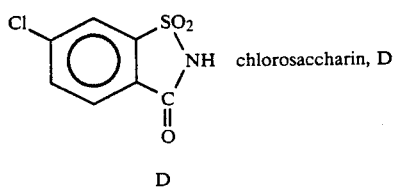

chlorosaccharin, D

Example 4 demonstrates that using 2-5-dichlorobenzenesulfonamide as a reactant produces a saccharin analogue salt and then chlorosaccharin, D, in accordance with the process of the present invention.

EXAMPLES 5-9

Carbonylation of 2-chloro-6-methylbenzenesulfonamide

In Examples 5-9, 2-chloro-6-methylbenzenesulfonamide, a catalyst including dppp and a base (with a molar ratio of 1:0.022:0.022:2) were heated in a solvent under CO pressure for a specified length of time. For these Examples, the same procedure was followed as afore described in Example 3. The reaction catalyst, solvent, pressure, temperature, time and yield for these Examples are as follows:

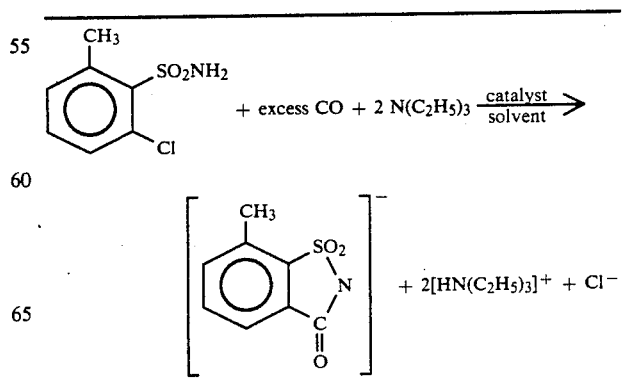

-continued

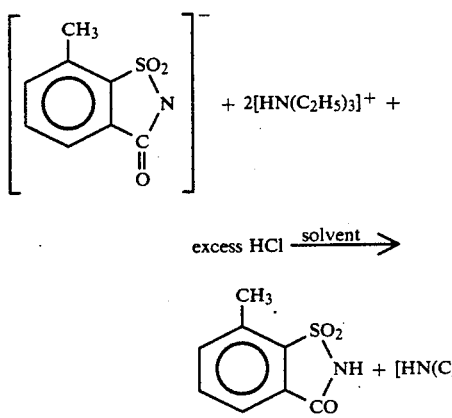

excess HCl $\xrightarrow{\text{solvent}}$

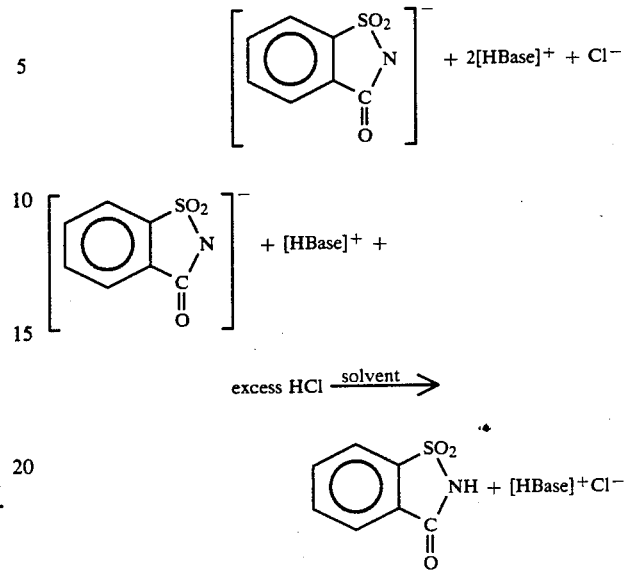

excess HCl $\xrightarrow{\text{solvent}}$

| Example | Catalyst | Solvent | Initial CO Pressure psia |
|---|---|---|---|
| 5 | Pd(CH₃CN)₄(BF₂) + dppp | dioxane | 70 |
| 6 | Pd(OCOCH₃)₂ + dppp | dioxane | 70 |
| 7 | Pd(OCOCH₃)₂ + dppp | C₆H₅CN | 60 |
| 8 | Pd(OCOCH₃)₂ + dppp | dioxane | 30 |
| 9 | Pd(OCOCH₃)₂ + dppp | dioxane | 60 (includes 14 psia air) |

| Example | Temp °C. | Time, hrs | Yield of Methylsaccharin % |
|---|---|---|---|
| 5 | 120 | 16 | >90 |
| 6 | 150 | 30 | >90 |
| 7 | 130 | 10 | >90 |
| 8 | 130 | 26 | >90 |
| 9 | 130 | 26 | >90 |

Like Example 3, Examples 5-9 used 2-chloro-6-methylbenzenesulfonamide as a reactant. Example 5 demonstrates that methylsaccharin salt, B, and methylsaccharin, C, can be produced like in Example 3, but with a different catalyst, specifically Pd(CH₃CN)₄(BF₄)₂ and dppp. Example 6 is similar to Example 3 using the same reactants, catalyst and solvent, but its yield was higher. Example 7 is similar to Example 3 using the same reactants and catalyst but its solvent was different and the initial CO pressure was slightly less. Still the reaction resulted in methylsaccharin salt, B, and then methylsaccharin, C. Examples 8 and 9 are similar to Example 3 using the same reactants, catalyst and solvent, but the initial CO pressure is different. Regardless of the significantly different initial CO pressures, a saccharin analogue salt and then a saccharin analogue resulted.

EXAMPLES 10-21

Carbonylation of 2-chlorobenzenesulfonamide

For Examples 10-21, the same procedure was followed as described in Example 3 above. In these Examples, the reaction shown in the following equations was performed using the catalysts, bases and solvents shown below, at the pressures and temperatures indicated, and for the time with the following yields.

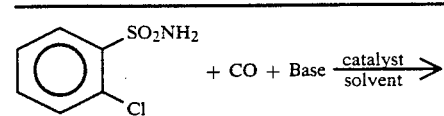

| Example | Catalyst | Base | Solvent |
|---|---|---|---|
| 10 | Pd(P(C₆H₅)₂CH₃)₄ | N(C₂H₅)₃ | dioxane |
| 11 | Pd(P(C₆H₅)₂CH₃)₄ | pyridine | dioxane |
| 12 | Pd(P(CH₃)₃)₄ | N(C₂H₅)₃ | dioxane |
| 13 | Pd(CH₃CN)₄(BF₄)₂ + dppp | N(C₂H₅)₃ | dioxane |
| 14 | Pd(CH₃CN)₄(BF₄)₂ + dppp | N(C₂H₅)₃ | dioxane |
| 15 | Pd(CH₃CN)₄(BF₄)₂ + dppp | N(C₂H₅)₃ | dioxane |
| 17 | Pd(OCOCH₃)₂ + dppp | N(C₂H₅)₃ | dioxane |
| 18 | Pd(OCOCH₃)₂ + dppp | N(C₂H₅)₃ | dioxane |
| 19 | Pd(OCOCH₃)₂ + dppp | CH₃CO₂Na | dioxane |
| 20 | Pd(OCOCH₃)₂ + dppp | N(C₂H₅)₃ | dioxane |
| 21 | Pd(OCOCH₃)₂ + dppp | N(C₂H₅)₃ | toluene |

| Example | Initial Co Pressure psia | Temp, °C. | Time, hrs | Yield of saccharin, % |
|---|---|---|---|---|
| 10 | 70 | 150 | 16 | 95 |
| 11 | 70 | 150 | 16 | 95 |
| 13 | 70 | 120 | 16 | 80 |
| 14 | 70 | 120 | 16 | 2 |
| 15 | 70 | 120 | 48 | 91 |
| 16 | 70 | 120 | 16 | 50 |
| 17 | 70 | 120 | 16 | 94 |
| 18 | 70 | 120 | 16 | 48 |
| 19 | 70 | 120 | 16 | 5 |
| 20 | 70 | 150 | 32 | 50 |
| 21 | 70 | 120 | 16 | 5 |

Examples 10-21 use 2-chlorobenzenesulfonamide as a reactant, like Example 1. In Example 1 a saccharin salt was produced. Whereas in Example 10 saccharin salt and then saccharin were produced. Example 11 is similar to Example 1, but Example 11 uses a different solvent. Example 12 is similar to Example 1, but had a greater initial CO pressure. Examples 13-15 used the catalyst of Example 2 with the reactants of Example 1. Further, Example 15 was performed longer than Example 13, for instance, resulting in a greater yield. Examples 17-21 used the catalyst of Examples 3 and 4 with the reactants of Example 1. Example 19 used a different base than used in Example 1. Example 21 used a different solvent than Example 1. Regardless of these differences, saccharin salt and saccharin were produced in all of Examples 10-21.

EXAMPLE 22

Carbonylation of 2-chlorobenzenesulfonamide with polystyrene-supported (dppp)PD(OCOCH$_3$)$_2$ 1. Preparation of dppp-supported by polystyrene.

To a suspension of 5.714 g (146 mmol) of potassium in 60 mL of dry tetrahydrofuran (THF) under nitrogen was added slowly a solution of 6.72 g (10 mmol) of (C$_6$H$_5$)$_2$P(CH$_2$)$_3$P(C$_6$H$_5$)$_2$ (prepared according to R. Uriarte, T. J. Mazanec, K. D. Tau and D. W. Meek, Inorg. Chem., Vol. 19, page 79 (1980)) in 40 mL of dry THF. The mixture turned yellow and a precipitate formed. After stirring at room temperature for two days, the suspension was transferred to a nitrogen glove box, the unreacted potassium was removed by decantation and the suspension was added to a rapidly stirred THF slurry containing 3.5 g of brominated polystyrene (1% crosslinked, containing 13.5% by weight bromine (Br), freshly prepared according to J. V. Minkiewicz, D. Milstein, J. Lieto, B. C. Gates and R. L. Albright, ACS Symp. Ser., No. 192, page 9 (1982)). After stirring for 72 hrs, the unreacted (C$_6$H$_5$)$_2$P(CH$_2$)$_3$P(C$_6$H$_5$)$_2$ was hyrolyzed with a deoxygenated acetone and water mixture having a 3 to 1 ratio by weight (3/1, 400 mL). The resulting resin beads were washed with 400 mL of the solvents acetone, water, benzene and methanol. 3.745 g of polymer were obtained after high vacuum drying for 3 days. Elemental analysis of the polymer showed: C 85.58%; H 7.40%; P 4.05%; and Br 0.52%.

2. Preparation of polystyrene-supported (dppp)Pd(OCOCH$_3$)$_2$.

To a solution of 1 g of palladium acetate in 100 mL of benzene in a nitrogen glove box were added 3.6 g of the dppp supported by polystyrene described above. After stirring at room temperature overnight, the polymer was filtered off and was washed well three times with 50 mL of benzene, three times with 50 mL of THF, three times with 50 mL of ether and again two times with 30 mL of benzene. 4.145 g of a brown polymer were obtained after vacuum drying for 2 days. Elemental analysis of the polymer indicated: C 74.4%; H 6.60%; P 3.27%; and Pd 8.86.%

3. Use of supported catalyst

A 90 mL glass pressure tube was charged in a nitrogen dry box with 2 g (10.4 mmol) of 2-chlorobenzenesulfonamide, 2.35 g (20.8 mmol) of triethylamine, 6 mL of dry acetonitrile (CH$_3$CN) and 130 mg of 1% crosslinked polystyrene-supported (dppp)Pd(OCOCH$_3$)$_2$ containing a 8.86% Pd (prepared as described above). The suspension was cooled to −80° C., evacuated and charged with 70 psia CO. After heating at 130° C. for 24 hours the tube was cooled to room temperature at which a pressure of 35 psia was observed. The pressure was released and the suspension was filtered. The resulting solid was washed three times with 5 mL of acetonitrile and the washings were added to the original solution. The solid was then washed three times with 10 mL of water, three times with 5 mL of methanol and three times with 5 mL of acetone and the washings were discarded to yield the polymeric catalyst which was dried under high vacuum. The solvent was removed from the filtrate under vacuum and HNMR and IR of the residue showed quantitative formation of the saccharin salt, A.

Example 22 demonstrates that saccharin salt, A, can be produced in accordance with the present invention using a catalyst supported on a polymer.

EXAMPLE 23

Carbonylation of 2-chlorobenzenesulfonamide with used polystyrene-supported (dppp)Pd(OCOCH$_3$)$_2$ Example 22 was repeated reusing the recovered polymeric catalyst and obtaining the same results. This Example demonstrates that saccharin salt, A, can be produced in accordance with the present invention reusing a catalyst supportedon a polymer which was previously used in a similar reaction.

COMPARATIVE EXPERIMENTS A-J

Attempted Carbonylation of 2-chlorobenzenesulfonamide

For Comparative Examples A-J, the same procedure was followed as described in Example 3 above. However, in these Comparative Examples, the following catalysts, bases and solvents were used at the following pressures and temperatures, for the following times resulting in the following yields:

| Experiment | Catalyst | Base | Solvent | Pressure psia | Temp. °C. | Time, hrs | Yield, % |
|---|---|---|---|---|---|---|---|
| A | Co$_2$(CO)$_8$ + ClCH$_2$CO$_2$CH$_3$ | K$_2$CO$_3$ | CH$_3$OH | 80 | 60 | 72 | 0 |
| B | Co$_2$(CO)$_8$ + ClCH$_2$CO$_2$CH$_3$ | CH$_3$ONa | CH$_3$OH | 80 | 60 | 72 | 0 |
| C | (C$_6$H$_5$CN)$_2$PdCl$_2$ | N(C$_2$H$_5$)$_3$ | DMF | 70 | 80 | 16 | 0 |
| D | (C$_6$H$_5$CN)$_2$PdCl$_2$ | CH$_3$ONa | CH$_3$CN | 90 | 100 | 16 | 0 |
| E | (C$_6$H$_5$CN)$_2$PdCl$_2$ | CH$_3$ONa | CH$_3$OH | 90 | 100 | 16 | 0 |
| F | (Pd(OCOCH$_3$)$_2$ + P(-o-tolyl)$_3$ where tolyl is C$_6$H$_4$CH$_3$ | N(C$_2$H$_5$)$_3$ | DMF | 70 | 120 | 16 | 0 |
| G | (dppe)NiCl$_2$ | N(C$_2$H$_5$)$_3$ | dioxane | 70 | 150 | 16 | 0 |
| H | Pd(CH$_3$CN)$_4$(BF$_4$)$_2$ | N(C$_2$H$_5$)$_3$ | dioxane | 70 | 120 | 16 | 0 |
| I | Pd(CH$_3$CN)$_4$(BF$_4$)$_2$ + dppp | CaO | dioxane | 70 | 120 | 16 | 0 |
| J | Pd(PC$_6$H$_5$)$_3$)$_4$ | N(C$_2$H$_5$)$_3$ | dioxane | 70 | 150 | 16 | 0 |

Comparative Experiments A and B demonstrate that catalyst complexes including Cobalt (Co) do not carbonylate 2-chlorobenzenesulfonamide. Comparative Experiments C-E and H show that catalysts including palladium, but not including phosphine, do not carbonylate 2-chloro-benzenesulfonamide. Comparative Experiment G shows that a catalyst complex including nickel (Ni), and no palladium, does not carbonylate 2-chlorobenzenesulfonamide. Comparative Experiments F and J show that palladium complexes containing (bound or added) PAr$_3$ ligands do not carbonylate 2-chlorobenzenesulfonamide. Comparative Experiment I shows that use of an insoluble base (CaO) does not result in carbonylation.

As is readily apparent to one skilled in the art, many modifications of the above described processes and compositions can be made without departing from the spirit and the scope of the invention herein.

What is claimed is:

1. A process for producing at least one salt of saccharin and/or saccharin analogues comprising reacting a compound selected from the group consisting of 2-chlorobenzenesulfonamide, 2-tosylatobenzenesulfonamide and mixtures thereof with carbon monoxide and base in the presence of solvent inert to the reactants and catalyst comprising at least one complex of Pd(0) or Pd(II) or Pd(IV) with at least one $PR_6R_7R_8$ or $R_9R_{10}P(CH_2)_nPR_{11}R_{12}$ ligand wherein:

$R_6$ is alkyl of 1 through 16 carbons;

$R_7$, $R_8$, $R_9$, $R_{10}$, $R_{11}$ and $R_{12}$ are independently selected from hydrogen, alkyl of 1 through 8 carbons, aryl of 6 through 14 carbons, or alkylaryl of 7 through 14 carbons; and n is 2, 3 or 4.

2. The process of claim 1, wherein the 2-chlorobenzenesulfonamide or 2-tosylatobenzenesulfonamide is of the formula:

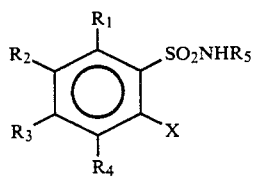

wherein:

X is Cl, or $O_3SC_6H_4CH_3$;

$R_1$, $R_2$, $R_3$ and $R_4$ are independently selected from hydrogen, alkyl of 1 through 9 carbons, F, Cl, Br, CN, $NO_2$, $OR_5$, $COR_5$, $CO_2R_5$, $SO_2R_5$ or aryl of 6 through 14 carbons; and $R_5$ is hydrogen, alkyl of 1 through 16 carbons or aryl of 6 through 14 carbons.

3. The process of claim 2, wherein $R_1$ and $R_2$, $R_2$ and $R_3$, or $R_3$ and $R_4$ may be a part of a fused aryl structure having 6 to 14 carbons.

4. The process of claim 3, wherein the fused aryl structure is

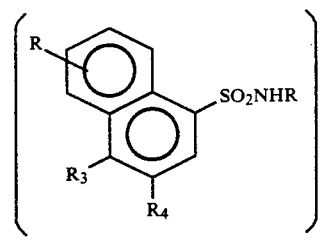

$R_5$ is hydrogen, alkyl of 1 through 16 carbons, aryl or alkylaryl, and R is independently $R_1$ through $R_4$.

5. The process of claim 2, wherein X is Cl.

6. The process of claim 2, wherein n is 3.

7. The process of claim 1, wherein the solvent is a polar solvent.

8. The process of claim 7, wherein the solvent is dioxane, benzonitrile or acetonitrile.

9. The process of claim 1, wherein the catalyst is supported by a polymer during the reaction.

10. The process of claim 9, wherein the catalyst is 1,3-bis(diphenylphosphino)propane bound to palladium acetate and the polymer is polystyrene.

11. A process for producing at least one salt of saccharin and/or saccharin analogues comprising reacting a compound selected from the group consisting of 2-chlorobenzenesulfonamide or 2-tosylatobenzenesulfonamide and mixtures thereof with carbon monoxide and base in the presence of solvent inert to the reactants and the catalyst of claim 8, whereby the catalyst is being used for at least the second time.

12. The process of claim 1, wherein the at least one Pd(O) complex consists essentially of $Pd(P(CH_3)(C_6H_5)_2)_4$ or $Pd(P(CH_3)_3)_4$.

13. The process of claim 1, wherein the at least one Pd(II) complex consists essentially of $Pd(CH_3CN)_4(BF_4)_2$ or $Pd(OCOCH_3)_2$.

14. The process of claim 1, wherein the at least one ligand consists essentially of 1,2-bis(diphenylphosphino)ethane, 1,3-bis(diphenylphosphino)propane, 1,4-bis(diphenyl-phosphino)butane, $PCH_3(C_6H_5)_2$ or $P(n-C_4H_9)_3$.

15. The process of claim 14, wherein the at least one ligand consists essentially of 1,3-bis(diphenylphosphino)propane.

16. The process of claim 1, wherein the reacted compound is 2-chlorobenzenesulfonamide.

17. The process of claim 1, wherein the 2-chlorobenzenesulfonamide consists essentially of 2-chloro-6-methylbenzene-sulfonamide or 2,5-dichlorobenzenesulfonamide.

18. The process of claim 1, wherein the 2-chlorobenzenesulfonamide or 2-tosylatobenzenesulfonamide is unsubstituted or substituted.

19. The process of claim 1, wherein the reaction is performed at a temperature from about 80° to about 250° C.

* * * * *